United States Patent [19]
Keogh

[11] Patent Number: 6,017,741
[45] Date of Patent: *Jan. 25, 2000

[54] PERIODATE OXIDATIVE METHOD FOR ATTACHMENT AND CROSSLINKING OF BIOMOLECULES TO MEDICAL DEVICE SURFACES

[75] Inventor: James R. Keogh, Maplewood, Minn.

[73] Assignee: Medtronic, Inc., Minneapolis, Minn.

[ * ] Notice: This patent is subject to a terminal disclaimer.

[21] Appl. No.: 09/257,542

[22] Filed: Feb. 24, 1999

Related U.S. Application Data

[63] Continuation of application No. 09/001,994, Dec. 31, 1997, Pat. No. 5,945,319.

[51] Int. Cl.$^7$ ........................ C12N 11/00; G01N 33/543; C07K 1/00; A61K 38/43
[52] U.S. Cl. .................. 435/174; 424/422; 424/94.1; 435/176; 435/177; 435/180; 435/181; 436/518; 436/524; 436/531; 436/532; 530/402; 530/810; 530/811; 530/815; 530/816
[58] Field of Search ..................... 435/174, 176, 435/177, 180, 181; 436/518, 524, 525, 528, 531, 532; 530/402, 810, 811, 812, 815, 816; 424/422, 94.1

[56] References Cited

U.S. PATENT DOCUMENTS

| | | | |
|---|---|---|---|
| 3,826,678 | 7/1974 | Hoffman et al. | 117/81 |
| 4,521,564 | 6/1985 | Solomon et al. | 525/54.1 |
| 4,600,652 | 7/1986 | Solomon et al. | 423/423.3 |
| 4,613,665 | 9/1986 | Larm | 536/20 |
| 4,642,242 | 2/1987 | Solomon et al. | 427/2 |
| 4,720,512 | 1/1988 | Hu et al. | 523/112 |
| 4,786,556 | 11/1988 | Hu et al. | 428/412 |
| 5,032,666 | 7/1991 | Hu et al. | 528/70 |
| 5,053,048 | 10/1991 | Pinchuk | 623/1 |
| 5,077,372 | 12/1991 | Hu et al. | 528/70 |
| 5,344,455 | 9/1994 | Keogh et al. | 623/11 |
| 5,362,852 | 11/1994 | Geoghegan | 530/345 |
| 5,728,420 | 3/1998 | Keogh | 427/2.12 |
| 5,821,343 | 10/1998 | Keogh | 530/402 |

OTHER PUBLICATIONS

R.G. Dickinson et al., "A New Sensitive and Specific Test for the Detection of Aldehydes: Formation of 6–Mercapto–3–substituted–s–traizolo[4,3–b]–s–tetrazines", *Chem. Commun.*, 1719–1720 (1970).

K.F. Geoghegan et al., "Site–Directed Conjugation of Non-peptide Groups to Peptides and Proteins via Periodate Oxidation of a 2–Amino Alcohol. Application to Modification at N–Terminal Serine", *Bioconjugate Chem.*, 3, 138–146 (1992).

A.S. Hoffman et al., A Covalent Binding of Biomolecules to Radiation–Grafted Hydrogels on Inert Polymer Surfaces,@ *Trans. Am. Soc. Artif. Intern. Organs*, 18, 10–18 (1972).

S. Holmes et al., AAmination of Ultra–high Strength Polyethylene using Ammonia Plasma,@ *Composites Science and Technology*, 38, 1–21 (1990).

Y. Ito et al., AMaterials for Enhancing Cell Adhesion by Immobilization of Cell–Adhesive Peptide,@ *J. Biomed. Mat. Res.*, 25, 1325–1337 (1991).

P.H. O=Farrell, AHigh Resolution Two–Dimensional Electrophoresis of Proteins,@ *J. Biol. Chem.*, 250, 4007–4021 (1975).

*Primary Examiner*—David M. Naff
*Attorney, Agent, or Firm*—Thomas F. Woods; Harold R. Patton

[57] ABSTRACT

Methods are provided for forming a coating of an immobilized biomolecule on a surface of a medical device to impart improved biocompatibility for contacting tissue and bodily fluids. A 2-aminoalcohol moiety of a biomolecule is oxidized with a periodate to an aldehyde moiety which is reacted with an amine moiety on the surface of a medical device to form an imine moiety, and the imine moiety is reduced to form an amine linkage immobilizing a coating of the biomolecule on the surface. Conversely, the biomolecule can contain the amine moiety and the 2-aminoalcohol moiety can be on the surface. In another method, a biomolecule coating containing an amine moiety and a 2-aminoalcohol moiety is immobilized on the surface of a medical device, and the 2-aminoalcohol moiety is oxidized with a periodate to an aldehyde moiety which reacts with the amine moiety to crosslink the coating. A crosslinked biomaterial may be formed by combining a periodate with two or more biomolecules containing amine moieties and 2-aminoalcohol moieties to oxidize the 2-aminoalcohol moieties to aldehyde moieties, and allowing the aldehyde moieties to react with the amine moieties. When a medical device surface containing amine moieties is present with the two or more biomolecules, some of the aldehyde moieties react with the amine moieties on the medical device surface resulting in both immobilizing and crosslinking of the biomolecules on the surface.

19 Claims, No Drawings

PERIODATE OXIDATIVE METHOD FOR ATTACHMENT AND CROSSLINKING OF BIOMOLECULES TO MEDICAL DEVICE SURFACES

CROSS-REFERENCE TO RELATED APPLICATION

The application is a continuation of application Ser. No. 09/001,994, filed Dec. 31, 1997, now U.S. Pat. No. 5,945,319.

BACKGROUND OF THE INVENTION

For many years, a number of medical devices (e.g., pacemakers, vascular grafts, stents, heart valves, etc.) that contact bodily tissue or fluids of living persons or animals have been developed, manufactured, and used clinically. A major problem with such articles is that their surfaces tend to adsorb a layer of proteins from tissues and fluids such as tears, urine, lymph fluid, blood, blood products, and other fluids and solids derived from blood. The composition and organization of this adsorbed protein layer is thought to influence, if not control, further biological reactions. Adverse biological reactions such as thrombosis and inflammation can diminish the useful lifetime of many devices.

Implantable medical devices also tend to serve as foci for infection of the body by a number of bacterial species. Such device-associated infections are promoted by the tendency of these organisms to adhere to and colonize the surface of the device. Consequently, it has been of great interest to physicians and the medical industry to develop surfaces that are less prone to promote the adverse biological reactions that typically accompany the implantation of a medical device.

One approach for minimizing undesirable biological reactions associated with medical devices is to attach various biomolecules to their surfaces for the attachment and growth of a cell layer which the body will accept. Biomolecules such as growth factors, cell attachment proteins, and cell attachment peptides have been used for this purpose. In addition, biomolecules such as antithrombogenics, antiplatelets, anti-inflammatories, antimicrobials, and the like have also been used to minimize adverse biomaterial-associated reactions.

A number of approaches have been suggested to attach such biomolecules. These approaches typically require the use of coupling agents such as glutaraldehyde, cyanogen bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to substrate surfaces.

For example, covalent attachment of biomolecules using water soluble carbodiimides is described by Hoffman et al., "Covalent Binding of Biomolecules to Radiation-Grafted Hydrogels on Inert Polymer Surfaces," *Trans. Am. Soc. Artif. Intern. Organs,* 18, 10–18 (1972); and Ito et al., "Materials for Enhancing Cell Adhesion by Immobilization of Cell-Adhesive Peptide," *J. Biomed. Mat. Res.,* 25, 1325–1337 (1991).

One type of biomolecule which is coupled to biomaterial surfaces with coupling molecules is protein. Proteins are polypeptides made up of amino acid residues. A protein comprising two or more polypeptide chains is an oligomeric protein. In general, established coupling procedures couple proteins to substrate surfaces through a protein's lysine amino acid residues which contain terminal amino groups. This method of binding has several inherent problems. For example, if a number of lysine residues are present on a protein's surface multiple attachments may occur. Multiple attachment sites may lead to multiple conformations of the protein on the biomaterial surface. The lack of coupling specificity may disrupt or destroy the biological activity of the protein being coupled. In addition, coupling molecules may add instability to the biomaterial surface and increase the prospect for burial of the attached protein in the coupling layer. Coupling molecules may also create nonspecific and undesirable crosslinks between protein molecules, thereby destroying the biological properties of the protein or they may create bonds amongst surface functional sites, thereby inhibiting attachment. The use of coupling molecules may also decrease the specificity for attachment of the protein to the biomaterial surface, thereby losing conformational control over the attachment process.

Thus, what is needed are alternative methods for attaching biomolecules to the substrate surface of a medical device, particularly methods that do not require the use of coupling molecules.

SUMMARY OF THE INVENTION

The present invention provides an improved method for covalently attaching a biomolecule to a substrate surface. More particularly, the present invention provides a method for making a medical device having at least one biomolecule immobilized on a biomaterial surface. The method includes the steps of: combining a periodate with a biomolecule comprising a 2-aminoalcohol moiety ($RCHOHCHNH_2R'$) to form an aldehyde-functional material (RCHO); combining the aldehyde-functional material with a material comprising a primary amine moiety ($R''NH_2$) to bond the two materials together through an imine moiety ($R''N=CHR$); and reacting the imine moiety with a reducing agent to form an immobilized biomolecule on a medical device biomaterial surface through a secondary amine linkage ($R''NH-CH_2R$).

A preferred method of the present invention comprises the steps of: combining a periodate with a biomolecule comprising a 2-aminoalcohol moiety to form an aldehyde-functional material in an aqueous solution having a pH between about 4 and about 9 and a temperature between about 0 and about 50 degrees Celsius; combining the aldehyde-functional material with a biomaterial surface comprising a primary amine moiety to immobilize the biomolecule on the substrate surface through an imine moiety; and reacting the imine moiety with a reducing agent to form an immobilized biomolecule on the biomaterial surface through a secondary amine linkage.

Another method of the present invention may be employed to crosslink biomolecules, located in solution or on biomaterial surfaces, comprising both a 2-aminoalcohol moiety and a primary amine moiety. This method includes the steps of: combining a periodate with the biomolecule to oxidize the 2-aminoalcohol moiety to form an aldehyde moiety; allowing the aldehyde moiety to combine with the amine moiety forming an imine moiety; and reacting the imine moiety with a reducing agent to form a secondary amine and a crosslinked material. Such a crosslinked material may be employed as a biomaterial or as a biomaterial coating. In addition, such a crosslinked material may be further modified to contain additional biomolecules. For example, aldehyde-containing biomolecules may be attached to residual amine moieties present in or on the surface of the crosslinked material.

Alternatively, amine-containing biomolecules may be attached to residual aldehyde moieties present in or on the surface of crosslinked material. Additionally, biomolecules coated onto a biomaterial surface may be crosslinked according to still another method of the present invention. Furthermore, biomolecules comprising amine moieties may be attached to biomaterial surfaces comprising 2-aminoalcohol moieties.

DETAILED DESCRIPTION OF THE INVENTION

As used in the specification and claims hereof, the following terms have the particular meanings and definitions set forth below.

I define the term "biomolecule" appearing herein as meaning any one or more of a biomolecule alone or a combination of different biomolecules.

I define the term "biomaterial" appearing herein as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains implanted in or in contact with the body. Biomaterials suitable for use in the present invention either include a 2-aminoalcohol moiety, an amine moiety, or both. Additionally, biomaterials may be fabricated by crosslinking biomolecules, comprising both a 2-aminoalcohol and a primary amine moiety, according to one method of the present invention.

I define the term "medical device" appearing herein as a device having surfaces that contact tissue, blood, or other bodily fluids in the course of their operation, which fluids are subsequently used in patients. This definition includes within its scope, for example, extracorporeal devices for use in surgery such as blood oxygenators, blood pumps, blood sensors, tubing used to carry blood and the like which contact blood which is then returned to the patient. The definition includes within its scope endoprostheses implanted in blood contact in a human or animal body such as vascular grafts, stents, pacemaker leads, heart valves, and the like that are implanted in blood vessels or in the heart. The definition also includes within its scope devices for temporary intravascular use such as catheters, guide wires, and the like which are placed into the blood vessels or the heart for purposes of monitoring or repair.

The present invention has the object of solving a number of problems associated with the use of medical devices. The present invention includes within its scope an oxidative process for covalently attaching biomolecules to biomaterial surfaces for use in medical devices. The present invention further provides an oxidative method for fabricating crosslinked biomaterials or crosslinked biomaterial coatings comprising biomolecules.

Biomolecules that possess carbon—carbon bonds bearing an amine moiety adjacent to a hydroxyl moiety ($RCHOHCHNH_2R'$) are oxidizable with periodate. A carbon—carbon bond bearing an amine moiety adjacent to a hydroxyl moiety is known as a 2-aminoalcohol moiety.

The 2-aminoalcohol moiety is oxidizable with periodate, which can be provided as periodic acid or salts thereof, such as sodium periodate, potassium periodate, or other alkali metal periodates. Typically, a stoichiometric amount of periodate is used to oxidize the 2-aminoalcohol moiety, although an excess could be used. Oxidation of such biomolecules forms reactive aldehyde moieties within the biomolecules.

The oxidation is carried out in an aqueous solution, preferably an aqueous buffered solution, at a temperature that does not destroy the biological properties of the biomolecule. Generally, buffers having a pH in a range between about 4 and about 9 can be used, with a pH between about 6 and about 8 desired for certain pH sensitive biomolecules. Generally, the oxidation is carried out at a temperature between about 0 and about 50 degrees Celsius, and preferably at a temperature between about 4 and about 37 degrees Celsius. Depending on the biomolecule, oxidation reactions can be carried out for as short as a few minutes to as long as many days. Commonly, oxidation is complete within 24 hours. Long-term oxidation reactions are preferably performed in the dark to prevent "overoxidation."

Treatment times and temperatures for the oxidation process tend to be inversely related. That is, higher treatment temperatures require relatively shorter treatment times. Time and temperature limitations of the present invention are generally governed by the biological stability of the biomolecules imparted by the oxidation process. Wide latitude may be employed in determining the optimum conditions for a particular system. Such conditions may be determined readily by one skilled in the art by routine experimentation upon examination of the information presented herein.

Subsequent to oxidation, the reaction solution may be stored prior to attachment to a substrate at about 4 degrees Celsius. Typically, the storage stability of the reaction solution at a neutral pH or slightly acidic pH may extend between about one and about fourteen days and sometimes even months when stored in the dark.

The resultant aldehyde moieties interact with sites on a biomaterial surface for covalent attachment of the biomolecules. These biomaterial surface attachment sites comprise amine moieties, which react with aldehyde moieties forming imines. The substrate surface to which the biomolecule is to be coupled should contain an adequate density of amine moieties for attaching the desired number of biomolecules.

Biomaterials of the present invention not containing amines on their surface may be aminated readily through a number of methods well known in the art. For example, amines may be provided by plasma treating materials with ammonia gas as found in Holmes and Schwartz, "Amination of Ultra-High Strength Polyethylene using Ammonia Plasma," *Composites Science and Technology*, 38, 1–21 (1990). Alternatively, amines may be provided by grafting acrylamide to the substrate followed by chemical modification to introduce amine moieties by methods well known to those skilled in the art, e.g., Hofmann rearrangement reaction. Polyvinylamines or polyalkylimines may also be covalently attached to polyurethane surfaces according to the method taught by U.S. Pat. No. 4,521,564 to Solomone et al. Alternatively, for example, aminosilane may be attached to the surface as set forth in U.S. Pat. No. 5,053,048 to Pinchuk, a grafted acrylamide-containing polymer may be attached by radiation grafting as set forth in U.S. Pat. No. 3,826,678 to Hoffman et al., a grafted N-(3-aminopropyl) methacrylamide-containing polymer may be attached by ceric ion grafting as set forth in U.S. Pat. No. 5,344,455 to Keogh et al.

Typically, when an aldehyde moiety (RCHO) reacts with a primary amine moiety (R'NH$_2$), an equilibrium is set up with the reaction product, which is a relatively unstable imine moiety (R'N=CHR). This coupling reaction may be carried out under the same conditions described above for the oxidation, which are designed to protect the biomolecule from damage. To stabilize the linkage between the biomolecule and the biomaterial surface, subsequent reductive alkylation of the imine moiety is carried out using reducing agents (i.e., stabilizing agents) such as, for example, sodium borohydride, sodium cyanoborohydride, and amine boranes, to form a secondary amine (R'NH—CH$_2$R). This reaction can also be carried out under the same conditions described above for the oxidation. Typically, however, the coupling and stabilizing reactions are carried out in a neutral or slightly basic solution and at a temperature between about 0 and about 50 degrees Celsius. Preferably, the pH is between about 6 and about 10, and the temperature is between about 4 and about 37 degrees Celsius, for the coupling and stabilizing reactions. These reactions (coupling and stabilizing) may be allowed to proceed for just a few minutes or for many hours. Commonly the reactions are complete (i.e., coupled and stabilized) within 24 hours.

Generally, biomolecules used according to this invention may be, for example an anticoagulant, an antithrombotic, a clotting agent, a platelet agent, an anti-inflammatory, an antibody, an immunoglobulin, a defense agent, an enzyme, a hormone, a growth factor, a neurotransmitter, a cytokine, a globular protein, a blood agent, a regulatory agent, a transport agent, a fibrous agent, a structural protein, a membrane protein, a cell attachment protein, a structural peptide, a membrane peptide, a cell attachment peptide, a proteoglycan, a toxin, an antibiotic, an antibacterial agent, an antimicrobial agent, a catalyst, a drug, a vitamin, an antibody, an antigen, a protein, a peptide, a DNA segment, a RNA segment, a nucleic acid, a ligand and a dye (which acts as a biological ligand). The biomolecules may be found in nature (naturally occurring) or may be chemically synthesized. As long as the biomolecule comprises a carbon—carbon bond bearing an amine moiety adjacent to a hydroxyl moiety (RCHOHCHNH$_2$R'), they may be attached to an aminated biomaterial surface by one method of the present invention. Specific examples of such biomolecules include proteins and peptides, chemically synthesized or naturally occurring, which comprise a N-terminal serine, a N-terminal threonine, or a 5-hydroxylysine (5-hydroxylysine is only known to occur naturally in collagen, but in principal may be placed anywhere in a synthetic peptide or protein). If the biomolecule comprises an amine moiety in addition to a 2-aminoalcohol moiety, it may be crosslinked to form a material which may be used as a biomaterial or as a biomaterial coating. Additionally, a biomolecule which comprises an amine moiety may be attached to a biomaterial surface comprising a 2-aminoalcohol moiety by another method of the present invention.

Biomolecules may be chemically synthesized by a number of methods well known to those skilled in the art. For example, a number of methods are know for synthesizing proteins or peptides from amino acids including solution (classical) synthesis methods and solid phase (e.g., SPPS) synthesis methods. Peptides of varying length may also be formed by the partial hydrolysis of very long polypeptide chains of proteins. Peptides are short chains constructed of two or more amino acids covalently joined through substituted amide linkages, termed peptide bonds. Two amino acids joined by a peptide bond forms a dipeptide. Three amino acids joined by two peptide bonds forms a tripeptide; similarly, there are tripeptides and pentapeptides. When there are many amino acids joined together, the structure is termed a polypeptide. In general, polypeptides contain less than 100 amino acid residues and proteins contain 100 or more amino acid residues.

Some biomolecules are susceptible to conformational changes when brought into contact with a hydrophobic substrate surface. These conformational changes can lead to the exposure of internalized nonpolar groups which may lead to hydrophobic interactions between the biomolecule and the surface. These hydrophobic interactions may cause the exclusion of water molecules that normally surround the biomolecule in solution. This exclusion of water molecules between the biomolecule and the surface strengthens the hydrophobic interaction and may cause further conformational change of the biomolecule. The degree of conformational change a biomolecule experiences may or may not destroy its biological properties. Therefore, one must take into account the hydrophobic nature of the substrate surface when attaching biomolecules which are prone to hydrophobic interactions. In such cases, it is preferred to create a hydrophilic environment on the biomaterial surface, thereby preventing any unwanted hydrophobic interactions between the biomolecule and the surface which may destroy the biological properties of the biomolecule.

There are a number of surface-derivatization techniques (e.g., grafting techniques) well known to those skilled in the art for creating hydrophilic substrate surfaces. For example, techniques based on ceric ion initiation, ozone exposure, corona discharge, UV irradiation and ionizing radiation ($^{60}$Co, X-rays, high energy electrons, plasma gas discharge) are known.

Substrates that may be modified according to one method of the present invention include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, human or animal protein or tissue such as bone, skin, teeth, collagen, laminin, elastin or fibrin, organic materials such as wood, cellulose, or compressed carbon, and other materials such as glass, and the like. Biomaterials of the present invention made using these materials may be coated or uncoated, and derivatized or underivatized.

One method of the invention may be used to modify substrates of any shape or form including tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind.

It will be understood by one of skill in the art that biomolecules comprising an amine moiety may be attached to a biomaterial surface comprising a 2-aminoalcohol moiety using a method of the present invention. Substrates that do not contain an adequate number of oxidizable attachment sites (i.e., 2-aminoalcohol moieties) may easily be derivatized by a number of methods well known to those skilled in the art.

It will also be understood by one of skill in the art that biomolecule coatings may be crosslinked using a method of the present invention. That is, biomolecule coatings that comprise both primary amine moieties and 2-aminoalcohol moieties may be crosslinked to provide desired physical and biological properties. The resultant imines formed following the crosslinking of the aldehydes (as a result of oxidation of the 2-aminoalcohol moieties) and amines may be stabilized using a reducing agent as described above.

For example, structural proteins may be crosslinked to form a material that may be used as a biomaterial or a biomaterial coating. Also, additional biomolecules, as described herein, may be attached to residual amine moieties contained in or on a fabricated crosslinked biomolecule biomaterial or biomaterial coating, as described herein. Alternatively, amine containing biomolecules may be attached to residual aldehyde moieties contained in or on a fabricated crosslinked biomolecule biomaterial or biomaterial coating, as described herein.

An example of a biomolecule of the present invention is collagen. Collagen, which is found in connective tissue, has special amino acids, one of which is 5-hydroxylysine which may be oxidized with a source of periodate, which may be provided as periodic acid or salts thereof, such as sodium periodate, potassium periodate, or other alkali metal periodates, to form a pendant aldehyde moiety. The resultant aldehyde moieties may be used to crosslink the collagen through bonds formed between the aldehydes and amines (lysine amino acid residues) contained on neighboring collagen molecules. The resultant imine bonds may then be reduced using a mild reducing agent like sodium borohydride, sodium cyanoborohydride, or amine boranes. These crosslinks may endow the collagen biomaterial or biomaterial coating with desirable biological and/or physical properties such as mechanical strength, anti-immunogenicity, biostability, among others, without the use of a coupling agent. Thus, the method of the present invention eliminates the need for using glutaraldehyde, a commonly used cytotoxic coupling agent, to crosslink the collagen to control its physical and biological properties.

The aldehyde moieties formed by oxidation of collagen may also be used to couple a variety of amine-containing biomolecules to the crosslinked collagen biomaterial or biomaterial coating. Also, the ability to create aldehyde moieties along collagen molecules enables them to be covalently attached to amine containing biomaterial surfaces. Such collagen-coated biomaterial surfaces may be used, for example, as cell seeding surfaces, cell binding surfaces, cell separating surfaces, tissue fixation, collagen-coated stents, collagen-coated vascular grafts or collagen glues.

Although the examples described below relate generally to treatment of polymeric films or tissue culture plates as substrate surfaces, those examples are merely illustrative and are intended to limit in no way the scope of the present invention.

EXAMPLE 1

Periodate Oxidation of a Peptide Containing a N-terminal Serine Amino Acid Residue Two biomolecules, a tripeptide made of three serine amino acid residues and a dipeptide made of two lysine amino acid residues, both obtained from Sigma Chemical Co. (St. Louis, Mo.), were incubated in sodium metaperiodate ($NaIO_4$) also obtained from Sigma Chemical Co. (St. Louis, Mo.). The tripeptide, 0.90 mmoles, was incubated in the dark while shaking at room temperature for 3 hours in 10 ml deionized water containing 1.2 mmoles $NaIO_4$. The resultant solution, 2.5 $\mu$l, was added to 2 ml of a solution containing 0.8 g NaOH, 0.2 g 4-amino-3-hydrazino-5-mercapto-1,2,4-triazole, which is available under the trade designation PURPALD from Sigma Chemical Co. (St. Louis, Mo.), in 20 ml deionized water, and shaken vigorously for 15 minutes at room temperature. The dipeptide, 0.72 mmoles, was incubated in the dark while shaking at room temperature for 3 hours in 10 ml deionized water containing 1.2 mmoles $NaIO_4$. The resultant solution, 10 $\mu$l (note that this amount is four times the amount used for the tripeptide), was then added to 2 ml PURPALD solution and shaken vigorously for 15 minutes at room temperature. The resultant solutions were then analyzed spectrophotometrically at 550 nm. Dickinson and Jacobsen, *Chem. Commun.*, 1719 (1970), described the specific and sensitive reaction of aldehydes with PURPALD to yield purple-to-magenta-colored 6-mercapto-5-triazolo-(4,3-b)-s-tetrazines which can be measured spectrophotometrically at 550 nm. Sample absorbances obtained at 550 nm were 0.04 for the dipeptide and 1.81 for the tripeptide, which indicates that only the tripeptide which contained an N-terminal serine was successfully oxidized using periodate. The dipeptide of the two lysine amino acids lacked a 2-aminoalcohol moiety, that is a carbon—carbon bond bearing an amine moiety adjacent to a hydroxyl moiety.

EXAMPLE 2

Periodate Oxidation of a Peptide Containing a N-terminal Threonine Amino Acid Residue A biomolecule, a dipeptide made of N-terminal threonine and leucine amino acid residues obtained from Sigma Chemical Co. (St. Louis, Mo.), was incubated in sodium metaperiodate ($NaIO_4$) also obtained from Sigma Chemical Co. (St. Louis, Mo.). The dipeptide, 4.3 mmoles, was incubated in the dark while shaking at room temperature for 3 hours in 10 ml deionized water containing 1.2 mmoles $NaIO_4$. The resultant solution, 10 $\mu$l, was added to 2 ml of the PURPALD solution described in Example 1 and shaken vigorously for 15 minutes at room temperature. After the 15 minutes of shaking at room temperature, the resultant solution was analyzed spectrophotometrically at 550 nm. Sample absorbance obtained at 550 nm was 0.62 indicating the periodate had successfully oxidized the N-terminal threonine amino acid present in the dipeptide, thereby forming an aldehyde moiety.

EXAMPLE 3

Periodate Oxidation of a Peptide Containing an N-terminal Serine Amino Acid Residue A biomolecule, a pentapeptide made of N-terminal serine, aspartic acid, glycine, arginine, and glycine amino acid residues obtained from Sigma Chemical Co. (St. Louis, Mo.), was incubated in sodium metaperiodate ($NaIO_4$) also obtained from Sigma Chemical Co. (St. Louis, Mo.). The pentapeptide, 0.01 mmoles, was incubated in the dark while shaking at room temperature for 3 hours in 2 ml deionized water containing 0.23 mmoles $NaIO_4$. The resultant solution, 10 $\mu$l, was added to 2 ml of the PURPALD solution described in Example 1 and shaken vigorously for 15 minutes at room temperature. After the 15 minutes of shaking at room temperature, the resultant solution was analyzed spectrophotometrically at 550 nm. Sample absorbance obtained at 550 nm was 0.74, indicating the periodate had successfully oxidized the N-terminal serine amino acid residue present in the pentapeptide, thereby forming an aldehyde moiety.

EXAMPLE 4

Oxidation of Collagen

The biomolecule, mouse collagen, type IV, obtained from Sigma Chemical Co. (St. Louis, Mo.), was oxidized with sodium metaperiodate ($NaIO_4$). Collagen type IV is known to mediate the attachment of epithelial, endothelial, myoblasts and nerve cells in vivo and in vitro. Two collagen solutions were prepared by i) mixing half a vial of collagen with 56 mg $NaIO_4$ in 5 ml deionized water and ii) mixing half a vial of collagen in 5 ml deionized water. Both solutions were incubated in the dark for 2 hours while shaking at room temperature. The resultant solutions, 100 $\mu l$ of each, were added to 2 ml the PURPALD solution described in Example 1 and shaken vigorously for 30 minutes at room temperature. After the 30 minutes of shaking at room temperature, the resultant solutions were analyzed spectrophotometrically at 550 nm. The PURPALD solution was used as the blank. Sample absorbances obtained at 550 nm were 0.03 for nonoxidized collagen and 0.25 for oxidized collagen, indicating the periodate had successfully oxidized the collagen, thereby forming aldehyde moieties.

EXAMPLE 5

Attachment of Periodate Oxidized Biomolecules to Aminated Substrates

One method for creating amines on substrate surfaces entails grafting substrate surfaces with acrylamide (AAm) and N-(3-aminopropyl)methacrylamide (APMA) monomers using ceric ($Ce^{IV}$) ions. The $Ce^{IV}$ ions create free radicals on ozone treated silicone and polystyrene surfaces and untreated polyurethane surfaces which initiate the graft copolymerization of the acrylamides. The amount of surface amination (the graft copolymerization of APMA and Mm) that takes place on the substrate surface may be measured via staining with ponceau S dye, a negatively charged dye molecule. This dye ionically associates with the primary amines on the aminated surface. Following grafting, a periodate oxidized biomolecule may be coupled to the amine containing derivatized substrate surface. A 2-aminoalcohol-containing biomolecule is first oxidized with sodium metaperiodate ($NaIO_4$) forming a reactive aldehyde moiety. The aldehyde moiety is then used to covalently attached the biomolecule to the primary amine moiety present on the substrate surface. Sodium cyanoborohydride ($NaCNBH_3$) is then used to stabilize the imine linkages. Specific procedures required for each of these steps are described below.

Polystyrene 24 well tissue culture plates were ozone treated by placing the culture plates in an ozone reaction vessel for 30 minutes while oxygen, which contained ozone, was flowing at a rate of 1.3 $cm^3$/min. The oxygen containing ozone was created by flowing the oxygen through a corona discharge apparatus, which exposed the flowing oxygen to an 8000V electrical potential. Following ozone treatment, the plates were soaked in nitrogen purged deionized water for 30 minutes at room temperature. Following the 30 minute soak in nitrogen purged deionized water, the plates were grafted with acrylamide (Mm) and N-(3-aminopropyl) methacrylamide (APMA) monomers using $Ce^{IV}$ ion. The grafting solution consisted of 40 g Mm, 10 g APMA, 50 g deionized water solution, and 20 g $Ce^{IV}$ ion solution. The $Ce^{IV}$ ion solution consisted of 2.74 g ceric ammonium nitrate and 3.15 g nitric acid in 50 ml deionized water. The plates were allowed to graft for 3 hours in a 65 degree Celsius nitrogen purged oven. Following grafting, the plates are rinsed vigorously with deionized water. The grafted plates were then tested with ponceau S dye. Following staining, the ponceau S dye was released from the surface using a 1% sodium dodecyl sulphate (SDS) solution and quantified spectrophotometrically at 520 nm. Sample absorbances obtained at 520 nm were 0.00 for nonderivatized plates and 1.44 for surface-derivatized plates. As the results demonstrate, the surface-derivatized plates contain primary amines on their surfaces.

The 2-aminoalcohol moiety of a peptide may be oxidized using the procedure of Example 1. Sodium cyanoborohydride (1 mg/ml) then is added to the oxidized peptide solution. The resultant solution then is immediately added to each of the amine containing surface-derivatized tissue culture plate wells (approximately 1 ml solution/well). The oxidized peptide is then incubated in the derivatized tissue culture plate wells overnight at room temperature. Following incubation, the wells are vigorously rinsed with phosphate buffered saline (PBS) solution.

Polyurethane film samples were cut into 1.4 cm diameter disks. Sample disks were grafted with Mm and APMA monomers using $Ce^{IV}$ ion. The sample disks were allowed to graft 1 hour at room temperature. Following grafting, the sample disks were rinsed vigorously with deionized water. Again, the 2-aminoalcohol moiety of a peptide can be oxidized as previously described. Sample disks are then exposed to the oxidized peptide solution. Sodium cyanoborohydride is then added (1 mg/ml) and the resultant solution and sample disks are incubated overnight at room temperature. Following incubation, the polyurethane sample disks are vigorously rinsed with PBS.

EXAMPLE 6

Crosslinking of Collagen

A biomolecule such as collagen, type IV, may be oxidized with sodium metaperiodate ($NaIO_4$). A collagen solution may be prepared by mixing half a vial of collagen with 56 mg $NaIO_4$ in 5 ml deionized. The solution may be incubated in the dark for 2 hours while shaking at room temperature. The oxidized collagen molecules are then allowed to form crosslinks, thereby bonding the molecules together through imine moieties. An imine moiety is formed from an aldehyde moiety of one collagen molecule reacting with an amine moiety of a neighboring collagen molecule. The imine linkages are then stabilized by reacting the imine moieties with sodium cyanoborohydride (1 mg/ml) to form secondary amine linkages. The resultant crosslinked material may be employed as a biomaterial or as a biomaterial coating.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

I claim:

1. A method of forming a crosslinked coating on a surface of a medical device, the coating imparting improved biocompatibility characteristics to the surface, the method comprising the steps of:
   (a) providing the medical device, the device having a suitable biomaterial forming the surface, the biomaterial comprising an amine moiety;
   (b) providing two or more biomolecules, the biomolecules comprising amine moieties and 2-aminoalcohol moieties, combining a periodate with the biomolecules to oxidize the 2-aminoalcohol moieties to form aldehyde moieties;
   (c) combining the biomolecules with the surface;
   (d) allowing the aldehyde moieties to combine with the amine moieties of the biomolecules and the amine moiety of the biomaterial to form imine moieties; and
   (e) reacting the imine moieties with a reducing agent to form amine linkages, the amine linkages immobilizing and crosslinking the biomolecules on the surface, the immobilized and crosslinked biomolecules forming the coating.

2. The method of claim 1, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

3. The method of claim 1, wherein the biomaterial comprises an amino acid residue.

4. The method of claim 1, wherein the biomolecule is selected from the group consisting of an antithrombotic agent, an anti-inflammatory, an antibody, an antigen, an immunoglobulin, an enzyme, a hormone, a neurotransmitter, a cytokine, a protein, a globular protein, a cell attachment protein, a peptide, a cell attachment peptide, a proteoglycan, a toxin, an antibiotic agent, an antibacterial agent, an antimicrobial agent, a polysaccharide, a carbohydrate, a fatty acid, a drug, a vitamin, a DNA segment, a RNA segment, a nucleic acid, a lectin, a dye and a ligand.

5. The method of claim 1, wherein the biomolecule is a naturally occurring biomolecule.

6. The method of claim 1, wherein the biomolecule is a chemically synthesized biomolecule.

7. The method of claim 1, wherein the biomolecule comprises an amino acid residue.

8. The method of claim 7, wherein the amino acid residue is selected from the group consisting of a N-terminal serine, a N-terminal threonine and a 5-hydroxylysine.

9. The method of claim 1, wherein the periodate comprises at least one of periodic acid, sodium periodate, alkali metal periodates, and potassium periodate.

10. The method of claim 1, wherein the periodate is combined with the 2-aminoalcohol moieties in an aqueous solution having a pH between about 4 and about 9.

11. The method of claim 1, wherein the periodate is combined with the 2-aminoalcohol moieties in an aqueous solution having a temperature between about 0 and about 50 degrees Celsius.

12. The method of claim 1, wherein the oxidizing step is performed in the absence of light.

13. The method of claim 1, wherein the biomolecules and the surface are combined in an aqueous solution having a pH between about 6 and about 10.

14. The method of claim 1, wherein the biomolecules and the surface are combined in an aqueous solution having a temperature between about 0 and about 50 degrees Celsius.

15. The method of claim 1, wherein the reducing agent comprises at least one of sodium borohydride, sodium cyanoborohydride, and amine borane.

16. The method of claim 1, wherein the reducing agent is combined with the imine moieties in an aqueous solution having a pH between about 6 and about 10.

17. The method of claim 1, wherein the reducing agent is combined with the imine moieties in an aqueous solution having a temperature between about 0 and about 50 degrees Celsius.

18. The method of claim 1, wherein at least a portion of the surface forms at least one of a tube, a rod, a membrane, a balloon, a bag and a sheet.

19. The method of claim 1, wherein the device comprises at least one of a biocompatible material selected from the group consisting of a metal, a titanium, a titanium alloy, a tin-nickel alloy, a shape memory alloy, an aluminum oxide, a platinum, a platinum alloy, a stainless steel, a MP35N stainless steel, a elgiloy, a stellite, a pyrolytic carbon, a silver carbon, a glassy carbon, a polymer, a polyamide, a polycarbonate, a polyether, a polyester, a polyolefin, a polyethylene, a polypropylene, a polystyrene, a polyurethane, a polyvinylchloride, a polyvinylpyrrolidone, a silicone elastomer, a fluoropolymer, a polyacrylate, a polyisoprene, a polytetrafluoroethylene, a rubber, a ceramic, a hydroxapatite, a human protein, a human tissue, an animal protein, an animal tissue, a bone, a skin, a tooth, a collagen, a laminin, a elastin, a fibrin, a wood, a cellulose, a compressed carbon and a glass.

* * * * *